(12) United States Patent
Finger et al.

(10) Patent No.: US 9,827,444 B2
(45) Date of Patent: Nov. 28, 2017

(54) RADIOACTIVE EPOXY IN OPHTHALMIC BRACHYTHERAPY

(71) Applicant: IP LIBERTY VISION CORPORATION, New York, NY (US)

(72) Inventors: Paul T. Finger, New York, NY (US); Toby Welles, Redding, CT (US); Jaime Simon, Angleton, TX (US)

(73) Assignee: IP LIBERTY VISION CORPORATION, New York, NY (US)

( * ) Notice: Subject to any disclaimer, the term of this patent is extended or adjusted under 35 U.S.C. 154(b) by 25 days.

(21) Appl. No.: 14/243,696

(22) Filed: Apr. 2, 2014

(65) Prior Publication Data

US 2015/0105601 A1  Apr. 16, 2015

Related U.S. Application Data

(60) Provisional application No. 61/891,360, filed on Oct. 15, 2013.

(51) Int. Cl.
*A61N 5/10* (2006.01)
*A61K 51/06* (2006.01)
*A61K 51/12* (2006.01)

(52) U.S. Cl.
CPC ............ *A61N 5/1017* (2013.01); *A61K 51/06* (2013.01); *A61K 51/1251* (2013.01); *A61N 2005/1019* (2013.01); *Y10T 29/49826* (2015.01)

(58) Field of Classification Search
CPC .. A61N 5/1001; A61N 5/1002; A61N 5/1007; A61N 5/1014; A61N 5/1015; A61N 5/1016; A61N 5/1027; A61N 5/1028; A61N 2005/1024; A61N 5/1017
See application file for complete search history.

(56) References Cited

U.S. PATENT DOCUMENTS

| | | | | |
|---|---|---|---|---|
| 5,489,425 | A | * | 2/1996 | Kruper, Jr. ........ A61K 47/48707 424/1.11 |
| 6,030,333 | A | * | 2/2000 | Sioshansi et al. ................ 600/3 |
| 6,152,869 | A | | 11/2000 | Park et al. |
| 6,231,495 | B1 | | 5/2001 | Denk |
| 6,443,881 | B1 | * | 9/2002 | Finger .............................. 600/1 |
| 2003/0144570 | A1 | * | 7/2003 | Hunter et al. .................... 600/1 |
| 2004/0197264 | A1 | * | 10/2004 | Schwarz et al. ............. 424/1.11 |
| 2008/0212738 | A1 | * | 9/2008 | Gertner .................. A61N 5/10 378/65 |
| 2010/0056843 | A1 | | 3/2010 | Fisher et al. |

OTHER PUBLICATIONS

International Search Report for PCT Application No. PCTUS1460204 dated Jan. 21, 2015.

* cited by examiner

*Primary Examiner* — Charles A Marmor, II
*Assistant Examiner* — Carrie R Dorna
(74) *Attorney, Agent, or Firm* — Mark S. Cohen; Pearl Cohen Zedek Latzer Baratz LLP (57) ABSTRACT

An ophthalmic radiation device using a polymeric radiation-source implemented as either a polymer molecularly bonded with a radioisotope or a polymeric encasement of a radioisotope.

21 Claims, 9 Drawing Sheets
(1 of 9 Drawing Sheet(s) Filed in Color)

RADIOACTIVE EPOXY IN OPHTHALMIC BRACHYTHERAPY

CROSS REFERENCE TO RELATED APPLICATIONS

This application claims the benefit of U.S. Ser. No. 61/891,360, filed on Oct. 15, 2013, which is incorporated by reference herein in its entirety.

FIELD AND BACKGROUND OF THE INVENTION

The present invention relates to the use of polymeric radiation-source in ophthalmic brachytherapy.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The subject matter regarded as the invention is particularly pointed out and distinctly claimed in the concluding portion of the specification. The invention, in regards to its features, components and their configuration, operation, and advantages are best understood with reference to the following description and accompanying drawings in which:

It will be appreciated that for clarity, elements shown in the figures may not be drawn to scale. Furthermore, where considered appropriate, reference numerals may be repeated among the figures to indicate corresponding elements.

DETAILED DESCRIPTION OF EMBODIMENTS OF THE PRESENT INVENTION

In the following detailed description, numerous details are set forth in order to provide a thorough understanding of the invention. However, it will be understood by those skilled in the art that the present invention may be practiced without these specific details and that well-known methods, procedures, and components have not been described in detail so as not to obscure the present invention.

Embodiments of the present invention are generally directed to an ophthalmic radiation device and, specifically, to embodiments of polymeric radiation-source used in the device.

The following terms will be used out through the document:

"Ophthalmic brachytherapy" refers to the use of radioactive materials in the treatment of, inter alia, sub-retinal neovascularization associated with Age-Related Macular Degeneration (AMG), and malignant and benign ocular tumors.

"Radiation-source", "source", "source material", "radioactive-source", "radioisotope" all refer to a radioactive material emitting therapeutic radiation.

"Radiation" includes any one or a combination of, inter alia, alpha particles, beta minus and beta plus particles, positrons, Auger electrons, gamma-rays, or x-rays.

"Holder" refers to a structure associated with a treatment wand of an ophthalmic radiation device. The holder is configured to support or to contain a glass radiation-source while a practitioner administers a therapeutic quantity of radiation.

"Radiation-source container" refers to radiation-source holders associated with brachytherapy treatment wand, shells associated with plaque radiation treatment, or other placement-related activities associated with ophthalmic brachytherapy.

"Wand", "treatment wand", "body of the wand", or "wand body" refer to an elongated ergonomic structure extending from a handle and supporting the holder at its distal end, according to embodiments. The wand is contoured to provide the optimal access, visibility, and control, and fatigue-preventive ergonomics for the surgeon. In a certain embodiment, the wand is light transmissive whereas in another embodiment the wand is implemented as non-light transmissive.

"Light guide" refers to substantially transparent solid bodies through which light propagation is directed in accordance with the surface geometry of the body.

"Connection configuration" includes plaque eyelets, or flex tabs, or any other structure providing support. It should be appreciated that support structure integral to both the body supported and the body providing the support is also considered a connection configuration.

"Radioactive polymer" refers to a radioisotope molecularly bonded to a polymer.

"Polymer" refers to molecules formed from repetitive monomers; carbon based or non-carbon based.

Figure 1:
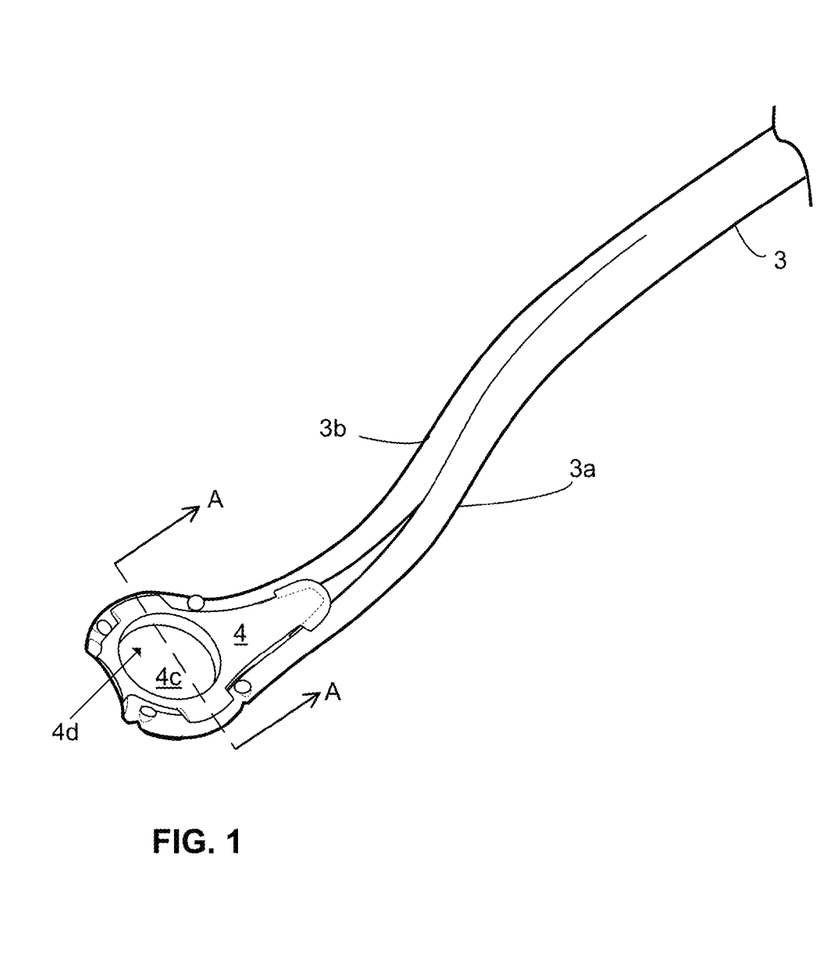
FIG. 1 is a schematic, perspective view of an unloaded radiation-source holder of a ophthalmic brachytherapy, according to an embodiment.

Turning now to the figures, FIG. 1 depicts a portion of a brachytherapy device in which a polymeric radiation-source may be held in a holder or container. Specifically, holder 4 has holding cavity 4d defined by its wall 4a (most clearly shown in FIG. 2) and floor 4c, according to an embodiment.

In a certain embodiment, holder 4 may include light transmitting elements 3a and 3b of treatment wand 3 as will be further discussed. Light transmitting embodiments 3a and 3b may be constructed of strong, substantially transparent polymeric material such as polycarbonate, polysulfone, or polyetherimide, or other material providing sufficient strength and transparency enabling light to propagate through wand 3.

Figure 2:
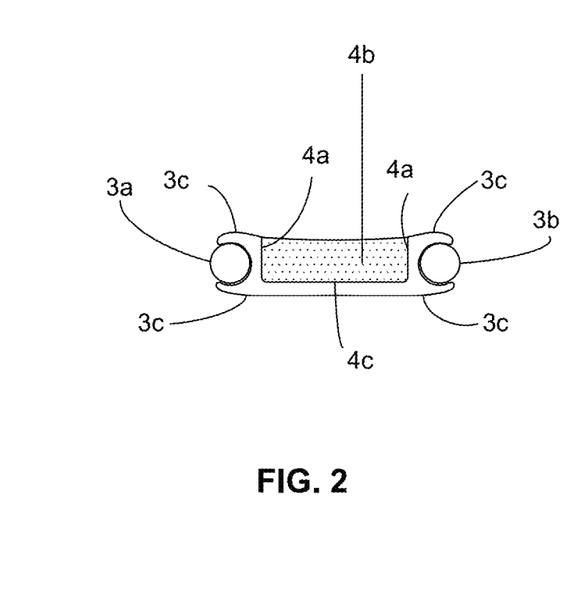
FIG. 2 is a schematic, cross-sectional view of the radiation-source holder of FIG. 1 along section line A-A shown in FIG. 1 loaded with a polymeric radiation-source, according to an embodiment.

FIG. 2 depicts holder 4 loaded with polymeric radiation-source 4b. Polymeric radiation-source 4b may be attached to holder 4 with various degrees of permanence, depending on the embodiment.

In one embodiment, polymeric radiation-source 4b is permanently connected to holder floor 4c or wall 4a by way of adhesive or fusion. Alternatively, polymeric radiation-source 4b may be permanently sealed inside holding cavity 4d shown in FIG. 1 with a cover (not shown) fused to wall 4a, or by other retention means.

Figure 2A:
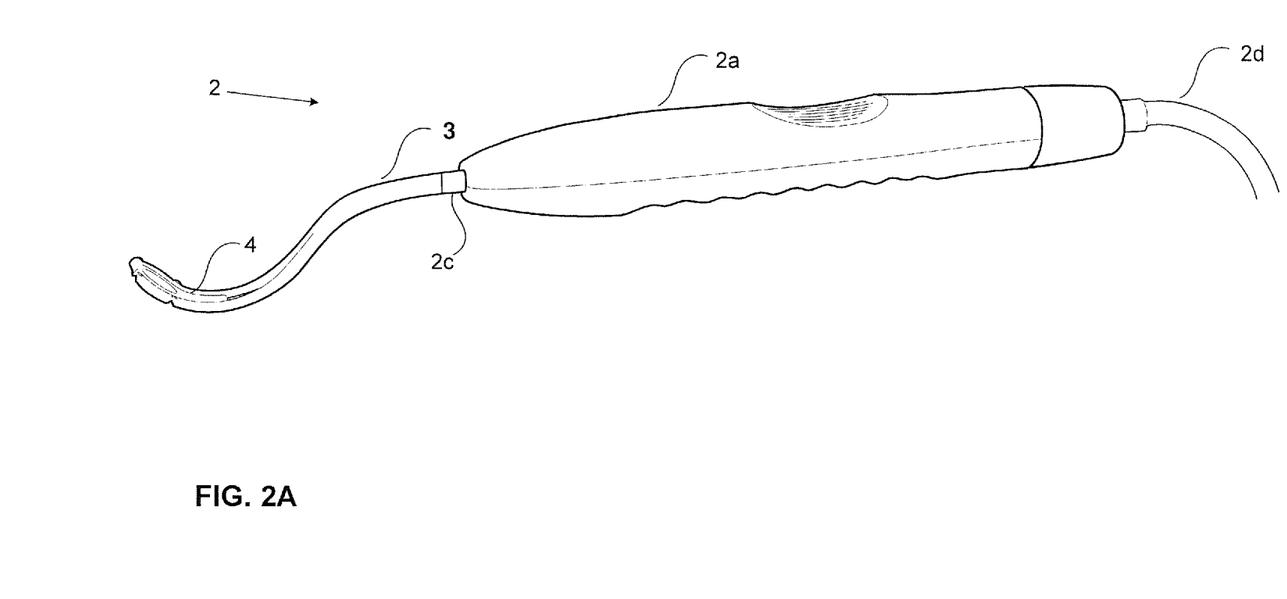
FIG. 2A is a general, schematic perspective view of an ophthalmic brachytherapy treatment device for the holder of FIG. 1, according to an embodiment.

Permanent connections of polymeric radiation-source 4b and holder 4 are used in embodiments having a disposable holder 4 or combination disposable treatment wand 3 and holder 4, or embodiments in which the entire ophthalmologic radiation device depicted in FIG. 2A is disposable. Flex tabs 3c releasably connect to light transmitting elements 3a and 3b of treatment wand 3 for embodiments in which the holder 4 is disposable. It should be appreciated that alternative connection configurations providing similar functionality are also included within the scope of the invention.

Appropriate construction materials of holder 4 include, inter alia, polycarbonate, metal or glass.

In another embodiment, polymeric radiation-source 4b is temporally connected by way of adhesive, or corresponding threading embedded in an outer surface of source 4b and wall 4a or floor 4c, or by way of a removable cover (not shown.) It should be appreciated that non-releasable connection configurations are also included within the scope of the invention.

FIG. 2A depicts an ophthalmologic radiation device to which the above-described treatment wand 3 connects. As shown, holder 4 is supported by wand 3 which in turn fastens to handle 2a via releasable connection configuration 2c, according to an embodiment.

In some embodiments, ophthalmologic radiation device 2 is fitted with a light pipe 2d for providing light that is transmitted through handle 2a and light transmitting elements 3a and 3b of treatment wand 3 as shown in FIG. 1.

Figure 2B:
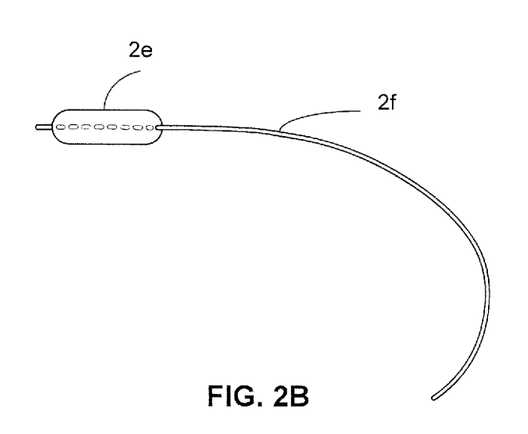
FIG. 2B is a schematic view of a polymeric radiation-source mounted on a wire applicator, according to an embodiment.

FIG. 2B depicts a polymeric radiation-source 2e disposed on an inert wire 2f to facilitate insertion through a catheter, according to an embodiment.

Figure 2C:
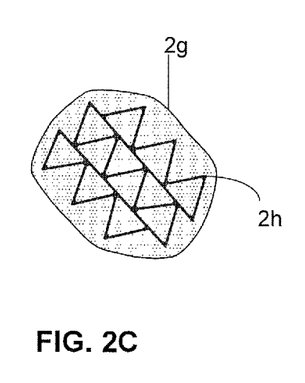
FIGS. 2C-2D are schematic views of polymeric radiation-sources with embedded wire support structure, according to embodiments.

FIG. 2C depicts a polymeric radiation-source 2g with an embedded support wire 2h configured into a triangular array to support various shapes in which polymeric source 2g may be formed, according to an embodiment.

Figure 2D:
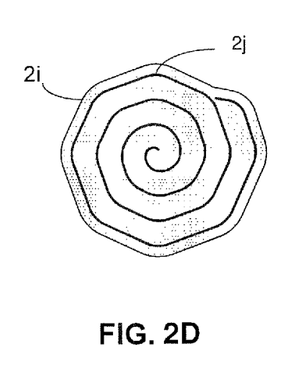

FIG. 2D depicts a polymeric radiation-source 2i with an embedded spiral support wire 2j also to support various shapes in which polymeric source 2i may be formed, according to an embodiment.

It should be appreciated that perforated metal, wire or plastic mesh, plastic strands, and plastic mesh armature are suitable substitutes for the above-described wire support structure and are also included within the scope of the present invention.

Figure 3A:
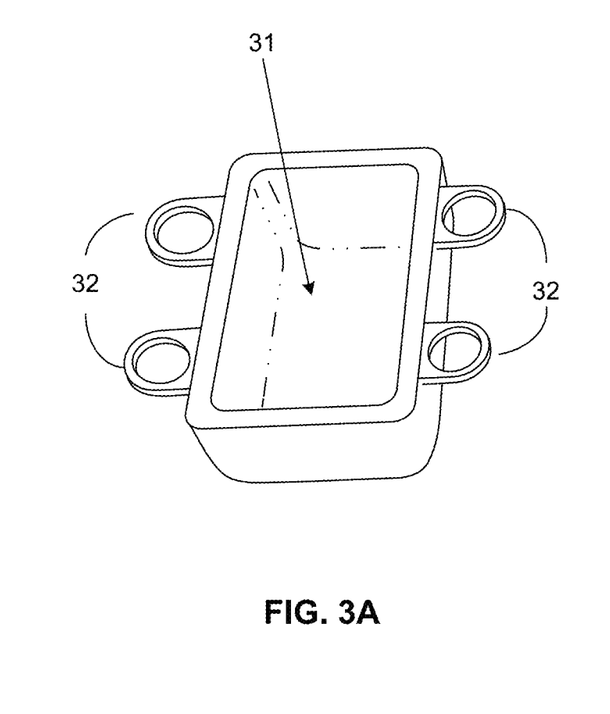
FIG. 3A is schematic, top view of an unloaded radiation-plaque, according to an embodiment.

FIG. 3A depicts a radiation-source container implemented as a radiation plaque or shell having a cavity 31 for receiving a polymeric radiation-source and eyelets 32 connected to the shell edge so as to enable suture attachment around a treatment area. Plaque 30 may be constructed from materials like, inter alia, gold, silver, steel, and polycarbonate. It should be appreciate that plaque 30 and any corresponding source 4b may be constructed to substantially match the contour of a treatment area.

Figure 3B:
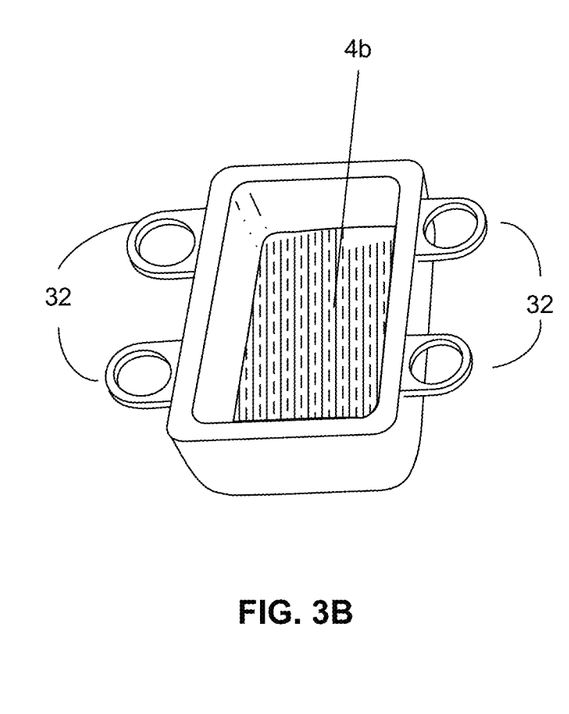
FIG. 3B is schematic, top view of a loaded radiation-plaque, according to an embodiment.

FIG. 3B depicts plaque 30 loaded with polymeric radiation-source 4b; various options of which will be discussed.

Figure 3C:
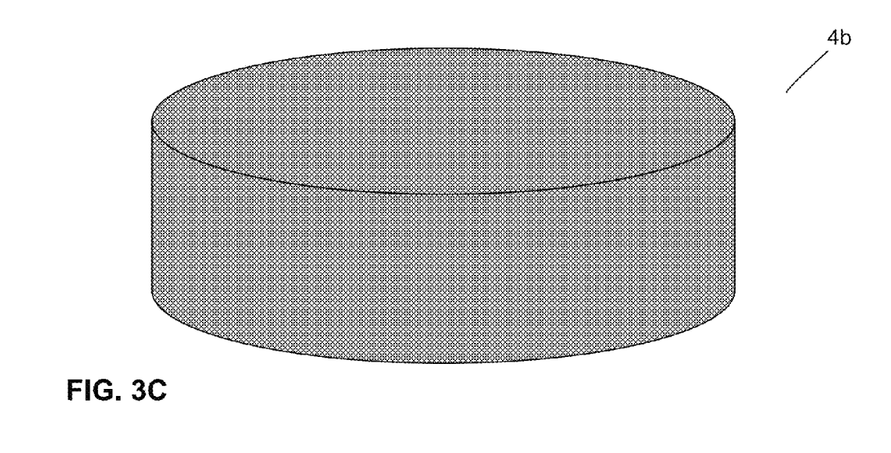
FIG. 3C is a schematic, perspective view of a polymeric radiation-source implemented as a disk, according to an embodiment.

FIG. 3C depicts a generally cylindrical, polymeric radiation-source 4b or disk having a thickness of approximately 0.2 mm to 5.0 mm thick and diameter between about 2.0 mm to 22.0 mm, according to an embodiment. It should be appreciated that polymeric radiation-source 4b can be formed into symmetrical or asymmetrical shapes of assorted surface geometries so as to modulate the radiation field in accordance with a particular need. For example, in certain embodiments a disk-shaped radiation-source may be implemented with a surface substantially matching the curvature of the eye globe.

During manufacture, image data of a treatment area may be derived from data provided by three dimensional medical imaging techniques like, inter alia, Magnetic Resonance Imaging (MRI), Three-Dimensional Ultrasound, Computed Axial Tomography (CAT or CT), Single-Photon Emission Computed Tomography (SPECT) or Positron Emission Tomography (PET), for example.

The data includes both surface geometry and shape data that can be used in a variety of manufacturing processes like, inter alia cutting, three-dimensional printing, or other rapid prototyping techniques like laser sintering, stereolithography, or fused filament fabrication. It should be appreciated that in a certain embodiment, these processes may be used to produce a mold for casting or forming polymeric radiation-source 4b.

In a certain embodiment, a radioactive polymer, from which the polymeric radiation-source 4b is formed, is produced by making a complex of a radioisotope and a bi-functional ligand and combining the complex with a polymer. When using metallic radioisotope, the bi-functional ligand is implemented as a bi-functional chelating agent having a chelant functional group that bonds to the metal radioisotope and a second functional group that bonds to the polymer.

Following is a sample method of producing a radioactive polymer and each of the test steps involved.

A suitable epoxy component like D.E.R.™ 331™ and suitable epoxy curing component like JEFFAMINE® D-230 Polyetheramine were acquired from epoxy distributors; their structures are shown below:

D.E.R.™ 331™

2,2'-(((propane-2,2-diylbis(4,1-phenylene))bis(oxy))bis(methylene))bis(oxirane)

JEFFAMINE® D-230

In order to examine the ability to prepare the epoxy parts without metals, formulations were prepared in 5 cm aluminum cups. The formula included adding 3.8 g of D.E.R.™ 331™ to the cup followed by the addition of 1.8 g of the amine. The two were stirred until mixed then heated in an oven at 75° C. for two hours. The parts were heated overnight in the same oven at 75° C. and showed no visual deformities.

In order to examine the ability to prepare parts with metals, a new mixture was prepared and metals were added to the mixture one with commercially available chelating agents and another without chelating agents. The two chelating agents selected included acetylacetone (AcAc) and a DOTA based bi-functional chelating agent (BFC). Acetylacetone was selected because it enhances the ability of metals to be incorporated into epoxy resins. The bi-functional chelating agent was chosen because it would make a neutral chelate with Y-90 and have an amine functional group that would react with the epoxy resin; the structures are shown below:

Acetylacetone

AminobenzylDO3A Chelator

When chelating agents were used, the metal was placed in a vial and chelating agent was added. The pH was adjusted to above 9. The part was prepared by adding 1.8 g of epoxy to the aluminum cup then adding the chelate solution and mixing. This was followed by adding 3.8 g of D.E.R.™ 331™ and stirring then heating at 75° C. for two hours.

Non-radioactive metal experiments were performed using 100 uL of 0.2 M yttrium solution. This was about 10 times what would need for 160 uCi. When yttrium with the amine were mixed without adding chelating agent, white turbidity appeared upon stirring and persisted even after adding D.E.R.™ 331™; but, turned clear upon curing the resin. 20 mg of acetylacetone which accounts for 5 times the amount of yttrium resulted in a clear solution when the amine was added. After heating the final part remained clear. There did not seem to be a pH adjustment needed when using acetylacetone.

When using five times the amount of DOTA-based chelating-agent, the mixture of amine was clear only when pH was adjusted prior to mixing. The turbidity of the materials when the pH was not adjusted thus implied that no chelate was formed until the pH was adjusted.

Afterwards tracer experiments were performed. Radioactive Lu-177 used to mimic Y-90 was purchased from Perkin Elmer. These two metals have a +3 charge and exhibit rare earth chemistry. Lu-177 has a longer half-life (6.73 days) and a gamma photon that can be used to trace the fate of the isotope. Ten mCi of Lu-177 in 5 uL of 0.5 M HCl was received. A volume of 95 uL of 0.5M HCl was added to make the solution 100 uCi/uL. One uL of Lu-177 per experiment was used.

Figure 3D:
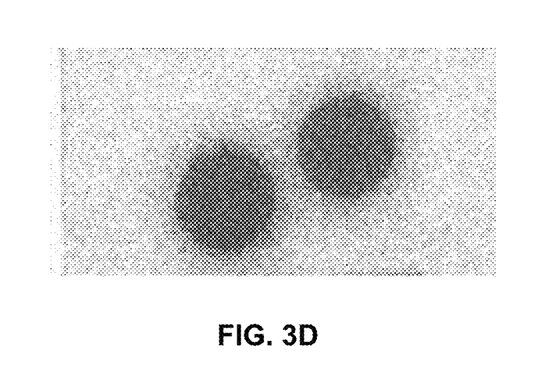
FIG. 3D are images of activity detected from experimental pucks containing Lu-177 obtained with phosphor imager during a tracer experiment.

Two separate parts, one containing no chelating agent and another containing 25 uL of acetylacetone were made. Both were cured at 75° C. to hard colorless material. After curing the parts were rubbed with a paper towel to determine if there was any removable contamination. Small amounts of radioactivity (<0.1%) were removable from the surface and additional rubbing resulted in no activity loss. An additional 0.5 grams of resin (a 10% coating) was added to cover the acetylacetone part. The puck was cured as before and the rubbing test was performed again. This showed no activity. Thus a second layer of epoxy was enough to prevent removable activity upon rubbing. The two parts were imaged using a collimator and a phosphor imager to determine the homogeneity of the activity. The results showed the activity evenly distributed in both pucks as shown in FIG. 3D.

Three additional pucks were prepared using tracer amounts of Lu-177 (100 uCi) and carrier added yttrium (enough to mimic 10× for a 160 uCi of Y-90).

The pucks were formed with the changes in chelating agent:
No chelating agent used.
Acetylacetone used.
DO3A based chelator (BFC) used.

They were prepared as described above and evaluated by for removable activity using a rubbing test. The results of the rubbing test are below given in percent of radioactivity removed appear below:

| Puck Label (FIG. 3E) | Puck | First Rub | Second Rub | Third Rub |
|---|---|---|---|---|
| 3f | No Chelant | 0.004 | 0.001 | 0.0005 |
| 3g | AcAc | 0.003 | 0.0005 | None |
| 3h | BFC | 0.001 | 0.0007 | 0.0004 |

Figure 3E:
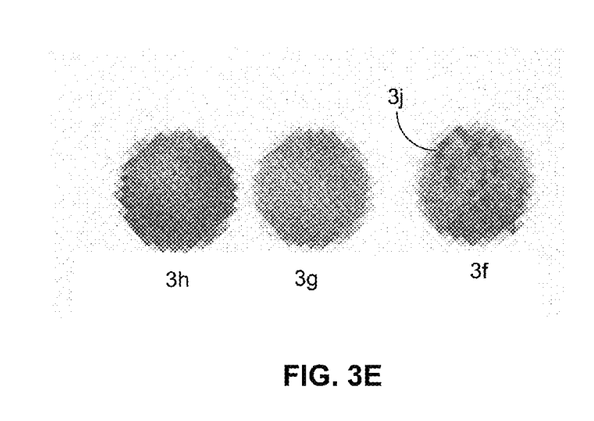
FIG. 3E are images of activity detected from experimental pucks containing Lu-177 and carrier added yttrium obtained by an imager during a carrier added experiment.

The imaging results for pucks 3f-3h appear in FIG. 3E. Puck 3f exhibits isolated pockets of activity 3j whereas pucks 3g-3h depict homogenous activity.

Metallic radioisotopes that may be chelated with a bi-functional chelating agent include, inter alia, $^{89}$Sr, $^{169}$Yb, $^{90}$Y, $^{192}$Ir, $^{103}$Pd, $^{177}$Lu, $^{149}$Pm, $^{140}$La, $^{153}$Sm, $^{186}$Re, $^{188}$Re, $^{166}$Ho, $^{166}$Dy.

$^{137}$Cs, $^{57}$Co, $^{169}$Er, $^{165}$Dy, $^{97}$Ru, $^{193m}$Pt, $^{195m}$Pt, $^{105}$Rh, $^{68}$Ni, $^{67}$Cu, $^{64}$Cu, $^{109}$Cd, $^{111}$Ag, $^{198}$Au.

$^{199}$Au, $^{201}$Tl, $^{175}$Yb, $^{47}$Sc, $^{159}$Gd, and $^{212}$Bi.

Following are additional examples of methods in which various types of radioisotopes may be bonded to various types of polymers. As noted above, embodiments of the radioactive polymer employ a bi-functional molecule capable of bonding with a radioisotope and also a polymer. If the radioisotope is a metal it can be attached via a chelating group; but if it is not, covalent attachment to the radioisotope can be employed.

Water-Soluble Bolton-Hunter Reagent

Sulfosuccinimidyl-3-(4-hydroxyphenyl)propionate

For example, this molecule can be first reacted with iodine (e.g. I-131) and an oxidizing agent such as chloramine-T or Iodogen to attach radioactive iodine to the phenol moiety. The left hand side has a reactive group that will react with amines to form amide linkages.

Polymer Example 1: Polyurethane

A glycol having a chelant functionality attached and a radioactive metal has been attached to the chelant functionality reacts with the polyurethane matrix to chemically bond the metallic radioisotope to the polymer. If the glycol has a phenolic group on it, it can be reacted with radioactive iodine then incorporated into the polyurethane in the same way. It should be appreciated that the radioisotope can also incorporate on the isocyanate portion of a polymer.

Polymer Example 2: Polycarbonate bisphenol A phosgene

The monomers are bisphenol A and phosgene; the phenol functional groups can be iodinated with radioactive iodine before the reaction with phosgene to form radio-iodinated polycarbonate. Similarly, for metallic radioisotopes, modify some of the bisphenol A molecules with a chelating agent having bonded metallic radioisotopes to attach radioactive metals to the polycarbonate.

Polymer Example 3: Polyethylene

A reactive monomer is prepared with an unsaturated end and a chelant or a phenol on the other side. React the monomer with the radioisotope first then incorporate it into a small amount of polymer that could be blended into the polymer.

It should be appreciated that the above-described methodology can be used to bond radioisotopes to a various types of polymers like, inter alia, polycarbonates as noted above, polyesters, and epoxies.

$^{32}$P, $^{33}$P, $^{77}$As may also be bonded to polymers in accordance to the general procedure described above.

Figure 4:
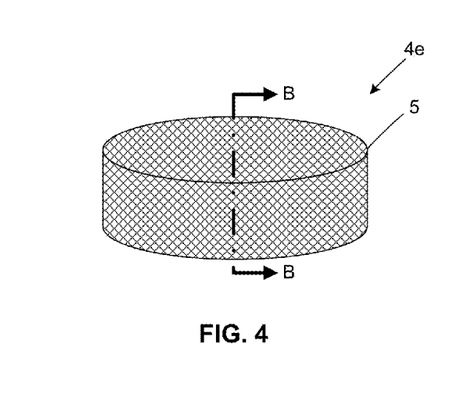
FIG. 4 is a schematic, perspective view of a polymeric radiation-source implemented as radioisotope encased in a polymeric encasement, according to an embodiment.
Figure 5:
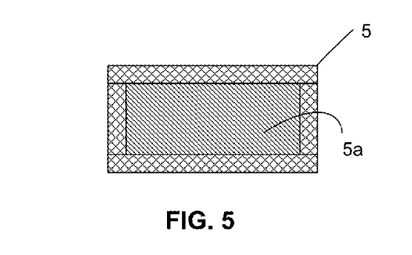
FIG. 5 is a schematic, perspective view of a polymeric radiation-source, implemented as a non-particulate radioisotopes encased in a polymeric encasement, according to an embodiment.
Figure 6:
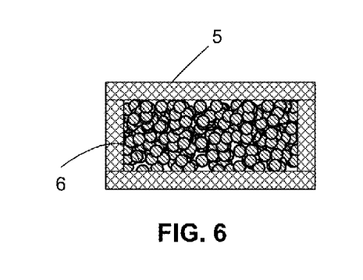
FIG. 6 is a schematic, cross-sectional view of the polymeric radiation-source of FIG. 4 implemented as neutron-activated, glass microspheres encased in a polymeric encasement, according to embodiments.
Figure 7:
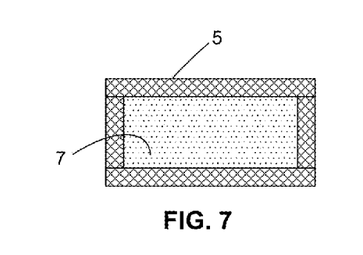
FIG. 7 is a schematic, cross-sectional view of the polymeric radiation-source of FIG. 4 implemented as particulate radioisotope encased in a polymeric encasement, according to an embodiment.

FIG. 4 depicts an embodiment of a radioactive polymeric-disk 4e implemented as a radioisotope encased in a polymeric encasement 5 as most clearly seen in the cross-sectional views along line B-B in FIGS. 5-7.

Polymeric encasement 5 is constructed from non-radioactive polymer in a certain embodiment and in another embodiment is constructed from a combination of radiation-permeable coating of metallic, glass, and polymeric materials to advantageously contain ablation, fragmentation, detachment, degradation, and selective attenuation of radiation emission.

Polymeric encasement 5 may be formed by any one or a combination of manufacturing processes including, inter alia, lamination, casting, drawing, forming, molding, blowing, adhesion, or extrusion.

FIG. 5 depicts an embodiment of radioisotope 5a encased inside of a polymeric encasement 5. Radioisotope 5a may be selected from any one or a combination of, inter alia, $^{89}$Sr, $^{169}$Yb, $^{32}$P, $^{33}$P, $^{90}$Y, $^{192}$Ir, $^{25}$I, $^{131}$I, $^{103}$Pd, $^{177}$Lu, $^{149}$Pm, $^{140}$La, $^{153}$Sm, $^{186}$Re,
$^{188}$Re, $^{166}$Ho, $^{166}$Dy, $^{137}$Cs, $^{57}$Co, $^{169}$Er, $^{165}$Dy, $^{97}$Ru, $^{193m}$Pt, $^{195m}$Pt, $^{105}$Rh,
$^{68}$Ni, $^{67}$Cu, $^{64}$Cu, $^{109}$Cd, $^{111}$Ag, $^{198}$Au, $^{199}$Au, $^{201}$Tl, $^{75}$Yb, $^{47}$Sc, $^{159}$Gd, $^{212}$Bi, and $^{77}$As.

In certain embodiments, radioisotope 5a is implemented as Auger emitters like, inter alia, 67Ga, 99 mTc, 111In, 123I, 125I, and 201Tl.

In certain other embodiments, radioisotope 5a is implemented as alpha-emitters like, inter alia, uranium, thorium, actinium, and radium, and the transuranic elements.

FIG. 6 depicts an embodiment of the encased radioisotope 4e of FIG. 4 in which the radioisotope is implemented as microspheres of neutron-activated glass microspheres 6 having an average diameter ranging between 0.2-10.0, according to an embodiment.

Radioactive microspheres 6 may be implemented from the materials like, inter alia, yttrium aluminosilicate, magnesium aluminosilicate, holmium-166, erbium-169, dysprosium-165, rhenium-186, rhenium-188, yttrium-90, or other elements on the periodic table. It should be appreciated that activation through bombardment of particles other than neutrons is also included within the scope of the present invention.

The neutron-activated glass 6 may be activated in cyclotron with high-energy particle bombardment. It should be appreciated that activation through bombardment of particles other than neutrons is also included within the scope of the present invention.

In a certain embodiment, glass microspheres 6 are formed from non-radioactive glass forming materials molecularly bonded with radioactive material. Examples of such radioactive materials that may be mixed together or chemically bonded to the glass include, inter alia, iodine-125, palladium-103, and strontium-90 to emit low energy gamma rays.

FIG. 7 depicts an embodiment of radioactive polymeric disk 4e of FIG. 4 in which the radioisotope is implemented as a particulate form 7 of the above noted radioisotopes.

The choice of a particular radioisotope or plurality of radioisotopes is defined by the particular therapeutic requirements.

Figure 7A:
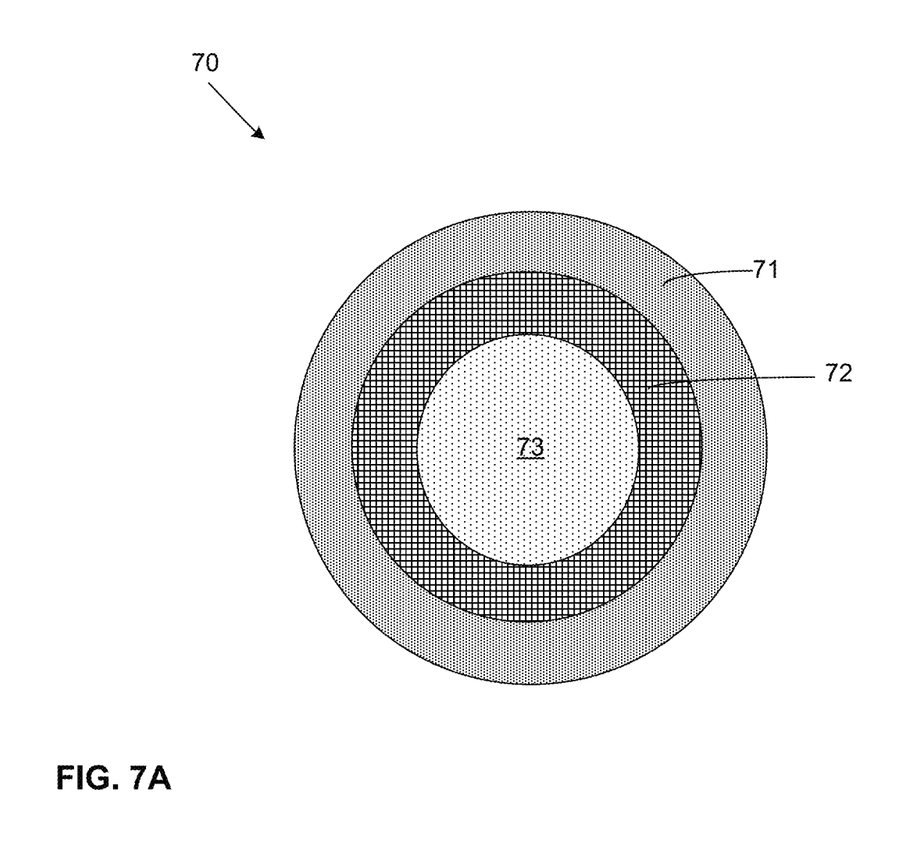
FIG. 7A is a schematic, top view of a polymeric radiation source containing multiple radioisotopes, according to an embodiment.

FIG. 7A is a schematic, top view of a polymeric radiation-source 70 containing multiple radioisotopes 71-73, that are configured to shape an intraocular dose distribution, according to an embodiment. It should be appreciated that various numbers of differing radioisotopes or identical isotopes of various concentrations that are configured non-concentrically are also included within the scope of the present invention. The various geometrical configurations advantageously facilitate selective exposure to various portions of a treatment area; e.g. a first portion receives a particular exposure, whereas second portion receives a different exposure.

Figure 8:
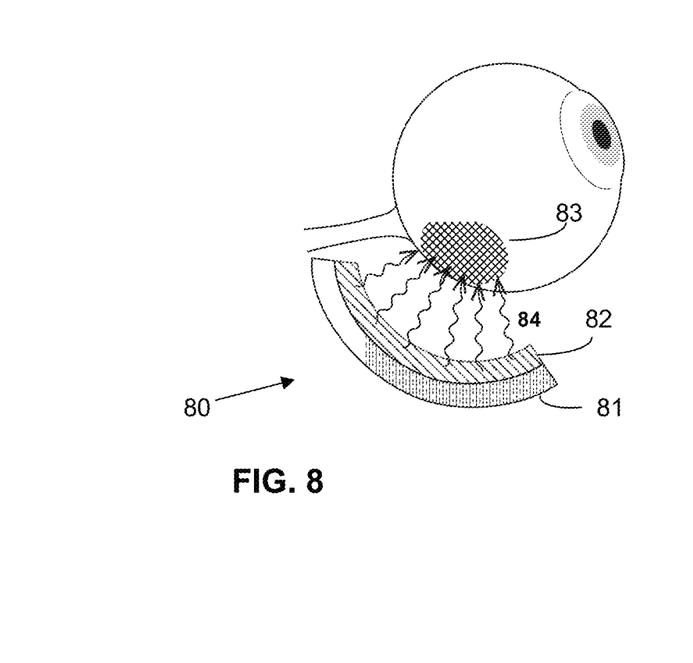
FIGS. 8 and 9 are schematic views of composite, polymeric radiation-sources having radioisotope and shielding layers, according to embodiments.
Figure 9:
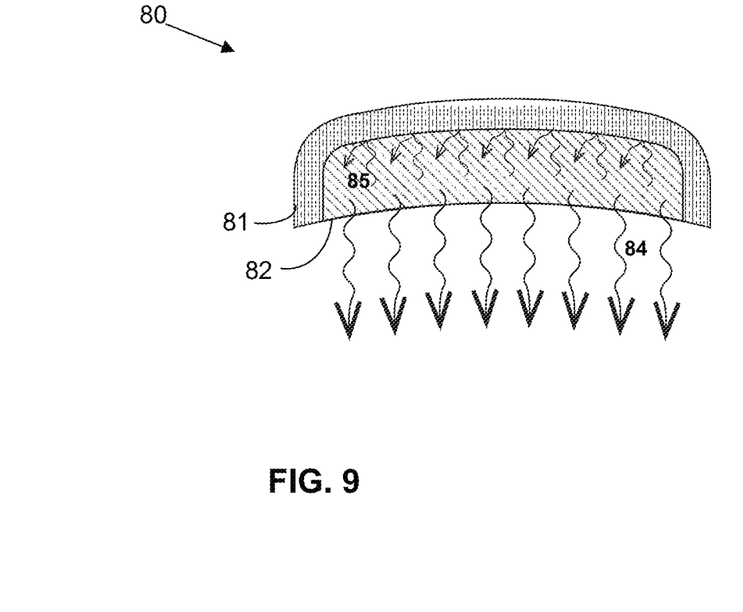

FIGS. 8 and 9 depict a radioactive source 80 implemented as a composite radiation-source having a glass, radioisotope layer 82 and shielding material layer 81.

FIG. 8 depicts shielding capacity of the composite radiation-source 80. As shown, radioisotope layer 82 directs radiation 84 towards treatment area 83 while shielding layer 81 simultaneously contains or reduces outward, radial radiation. Suitable shielding materials include heavy metals like, inter alia, gold, platinum, steel, tungsten, lead or non-metallic materials like polymeric materials or fluids; the particular material chosen in accordance with the radiation type being shielded.

FIG. 9 depicts reflective capacity of shielding layer 81 of the composite radiation-source 80. As shown, radioisotope layer 82 directs radiation 84 towards treatment area and shielding layer 81 shapes the radiation distribution 85 towards the target area thereby enhancing the administration of therapeutic radiation, according to an embodiment.

It should be appreciated that in many embodiments composite, glass-radiation-sources and shielding material inherently shield and reflect simultaneously. Construction methods described above may also be employed to construct composite glass, radiation-sources.

Figure 10:
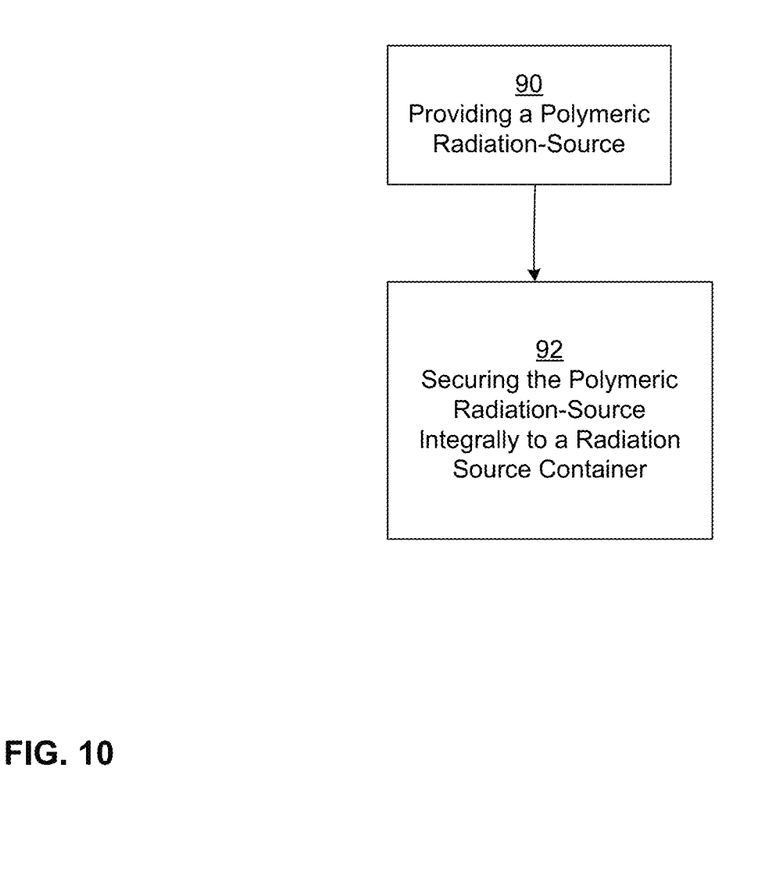
FIG. 10 is a flow chart depicting a method for a non-limiting method for loading a polymeric radiation-source into an ophthalmic radiation device.

FIG. 10 is a flow chart for a non-limiting method for loading a radiation-source into an ophthalmic radiation device. Specially, in step 90, a polymeric radiation-source is provided and in step 92 and the polymeric radiation-source is integrally secured to a radiation-source container.

It should be appreciated that any combination of the various features and methods are also included within the scope of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An ophthalmic, brachytherapy radiation device for delivering a therapeutic dose of radiation to diseased ocular tissue, the radiation device comprising:
    a non-retractable, radiation-source container:
    and
    a polymeric radiation-source disposed in the container, the polymeric radiation-source having a shape and a surface geometry formed in accordance with three-dimensional imaging data of an ocular treatment volume and a radiation profile of one or more radioisotopes employed in the polymeric radiation-source such that therapeutic radiation is adapted to be directed into the ocular treatment volume.

2. The ophthalmic radiation device of claim 1, wherein the polymeric radiation-source includes a metallic radioisotope chelated to a non-heterocyclic amine.

3. The ophthalmic radiation device of claim 2, wherein the metallic radioisotope is selected from the group consisting of $^9$Sr, $^{169}$Yb, $^{90}$Y, $^{192}$Ir, $^{103}$Pd, $^{177}$Lu, $^{149}$Pm, $^{140}$La, $^{153}$Sm, $^{186}$Re, $^{188}$Re, $^{166}$Ho, $^{166}$Dy, $^{137}$Cs, $^{57}$Co, $^{169}$Er, $^{165}$Dy, $^{97}$Ru, $^{193m}$Pt, $^{195m}$Pt, $^{105}$Rh, $^{68}$Ni, $^{67}$C, $^{64}$Cu, $^{109}$Cd, $^{111}$Ag, $^{198}$Au, $^{199}$Au, $^{201}$Tl, $^{175}$Yb, $^{47}$Sc, $^{159}$Gd, and $^{212}$Bi.

4. The ophthalmic radiation device of claim 1, wherein the polymeric radiation-source includes non-metallic radioisotopes.

5. The ophthalmic radiation device of claim 1, herein polymeric radiation-source has at least one embedded support wire.

6. The ophthalmic radiation device of claim 1, wherein the container includes a radiation plaque.

7. The ophthalmic radiation device of claim 1, wherein the polymeric radiation-source is implemented with radiation-permeable metallic coating.

8. The ophthalmic radiation device of claim 7, wherein the non-retractable radiation-source container includes a plurality of releasable connection configurations.

9. The ophthalmic radiation device of claim 8, wherein the releasable connection configurations are selected from the group consisting of plaque eyelets and flex tab configurations.

10. The ophthalmic radiation device of claim 1, wherein the polymeric radiation-source is implemented as a radioisotope at least partially encased in a non-radioactive polymeric encasement.

11. The ophthalmic radiation device of claim 10, wherein the radioisotope is implemented as radiation emitters selected from the group consisting of alpha particle emitters, beta minus and beta plus emitters, Auger electron emitters, gamma-ray emitters, and x-rays emitters.

12. The ophthalmic radiation device of claim 10, wherein the radioisotope is selected from the group consisting of $^{89}$Sr, $^{169}$Yb, $^{32}$P, $^{33}$P, $^{90}$Y, $^{192}$Ir, $^{125}$I, $^{131}$I, $^{103}$Pd, $^{177}$Lu, $^{149}$Pm, $^{140}$La, $^{153}$Sm, $^{186}$Re, $^{188}$Re, $^{166}$Ho, $^{166}$Dy, $^{137}$Cs, $^{57}$Co, $^{169}$Er, $^{165}$Dy, $^{97}$Ru, $^{193m}$Pt, $^{195m}$Pt, $^{105}$Rh, $^{68}$Ni, $^{67}$Cu, $^{64}$Cu, $^{109}$Cd, $^{111}$Ag, $^{198}$Au, $^{199}$Au, $^{201}$Tl, $^{175}$Yb, $^{47}$Sc, $^{159}$Gd, $^{212}$Bi, and $^{77}$As.

13. The ophthalmic radiation device of claim 12, wherein the radioisotope is implemented as a particulate.

14. The ophthalmic radiation device of claim 10, wherein the radioisotope includes neutron-activated glass selected from the group consisting of yttrium aluminosilicate, magnesium aluminosilicate, holmium-166, erbium-169, dysprosium-165, rhenium-186, rhenium-188, and yttrium-90.

15. A method for loading a brachytherapy radiation-source into an ophthalmic radiation device, the method comprising:

providing a non-retractable radiation-source container; and securing the polymeric, brachytherapy radiation-source to the radiation-source container, the polymeric radiation-source having a shape and a surface geometry formed in accordance with three-dimensional imaging data of an ocular treatment volume and a radiation profile of one or more radioisotopes employed in the polymeric radiation-source such that therapeutic radiation is directed into the ocular treatment volume.

16. The method of claim 15, wherein the polymeric radiation-source includes a metallic radioisotope chelated to a non-heterocyclic amine.

17. The method of claim of claim 16, wherein the metallic radioisotope is selected from the group consisting of $^{9}Sr$, $^{169}Yb$, $^{90}Y$, $^{192}Ir$, $^{103}Pd$, $^{177}Lu$, $^{149}Pm$, $^{140}La$, $^{153}Sm$, $^{186}Re$, $^{188}Re$, $^{166}Ho$, $^{166}Dy$, $^{137}Cs$, $^{57}Co$, $^{169}Er$, $^{165}Dy$, $^{97}Ru$, $^{193m}Pt$, $^{195m}Pt$, $^{105}Rh$, $^{68}Ni$, $^{67}C$, $^{64}Cu$, $^{109}Cd$, $^{111}Ag$, $^{198}Au$, $^{199}Au$, $^{201}Tl$, $^{175}Yb$, $^{47}Sc$, $^{159}Gd$, and $^{212}Bi$.

18. The method of claim 15, wherein the polymeric radiation-source is implemented as a non-radioactive polymeric encasement of neutron-activated glass.

19. The method of claim 18, wherein the neutron-activated glass is selected from the group of materials consisting of yttrium aluminosilicate, magnesium aluminosilicateholmium-166, erbium-169, dysprosium-165, rhenium-186, rhenium-188, and yttrium-90.

20. The method of claim 15, wherein the polymeric radiation-source includes a radioisotope selected from the group consisting of $^{89}Sr$, $^{169}Yb$, $^{32}P$, $^{33}P$, $^{90}Y$, $^{192}Ir$, $^{125}I$, $^{131}I$, $^{103}Pd$, $^{177}Lu$, $^{149}Pm$, $^{140}La$, $^{153}Sm$, $^{186}Re$, $^{188}Re$, $^{166}Ho$, $^{166}Dy$, $^{137}Cs$, $^{57}Co$, $^{169}Er$, $^{165}Dy$, $^{97}Ru$, $^{193m}Pt$, $^{195m}Pt$, $^{105}Rh$, $^{68}Ni$, $^{67}Cu$, $^{64}Cu$, $^{109}Cd$, $^{11}Ag$, $^{198}Au$, $^{199}Au$, $^{201}Tl$, $^{175}Yb$, $^{47}Sc$, $^{159}Gd$, $^{212}Bi$, and $^{77}As$.

21. The method of claim 15, further comprising releasably connecting the radiation-source container to a treatment wand.

* * * * *